(12) United States Patent
Scaife

(10) Patent No.: US 11,464,679 B2
(45) Date of Patent: Oct. 11, 2022

(54) HIGH SPEED SAP PARTICLE APPLICATOR

(71) Applicant: FMCG Consulting Ltd., Singapore (SG)

(72) Inventor: Martin Scaife, Singapore (SG)

(73) Assignee: FMCG CONSULTING, Singapore (SG)

( * ) Notice: Subject to any disclaimer, the term of this patent is extended or adjusted under 35 U.S.C. 154(b) by 0 days.

(21) Appl. No.: 15/319,739

(22) PCT Filed: Jun. 16, 2015

(86) PCT No.: PCT/EP2015/063501
§ 371 (c)(1),
(2) Date: Dec. 16, 2016

(87) PCT Pub. No.: WO2015/193332
PCT Pub. Date: Dec. 23, 2015

(65) Prior Publication Data
US 2017/0128276 A1 May 11, 2017

(30) Foreign Application Priority Data

Jun. 16, 2014 (GB) ..................................... 1410720

(51) Int. Cl.
*B05D 1/22* (2006.01)
*A61F 13/15* (2006.01)
*B05D 1/24* (2006.01)
*A61F 13/00* (2006.01)

(52) U.S. Cl.
CPC .......... *A61F 13/15658* (2013.01); *B05D 1/24* (2013.01); *A61F 2013/15821* (2013.01)

(58) Field of Classification Search
CPC ..... A61F 13/15658; A61F 2013/15821; B05D 1/24
USPC .................................................. 222/478, 482
See application file for complete search history.

(56) References Cited

U.S. PATENT DOCUMENTS

| 5,156,902 A | 10/1992 | Pieper et al. |
| 7,838,722 B2 | 11/2010 | Blessing et al. |
| 8,646,506 B2 | 2/2014 | Ukegawa et al. |
| 2012/0312491 A1* | 12/2012 | Jackels ............. A61F 13/15658 162/297 |

FOREIGN PATENT DOCUMENTS

| EP | 1621166 B1 | 9/2010 | |
| EP | 2412343 A1 * | 2/2012 | ....... A61F 13/15658 |

(Continued)

*Primary Examiner* — Alexander M Weddle
(74) *Attorney, Agent, or Firm* — Jordan IP Law, LLC

(57) ABSTRACT

The present invention relates to an apparatus and a method of applying a single SAP (Super Adsorbent Polymer) type granules or multiple SAP types at high speed in a continuous or intermittent 2-dimensional or 3-dimensional profile via volumetric or gravimetric metering onto a receiving system such as a carrier layer and/or into an air stream for use in an absorbent article, particularly diapers for babies or adults, training pants, pull-up diapers (diaper pants), sanitary napkins, panty liners or the like. These articles typically comprise of a carrier layer with the SAP particles and/or a mixed SAP and fiber core together with further layers, making up the complete article.

7 Claims, 22 Drawing Sheets

(56) References Cited

FOREIGN PATENT DOCUMENTS

| | | |
|---|---|---|
| EP | 2412343 A1 | 2/2012 |
| EP | 2491908 A1 | 8/2012 |
| WO | 2012/048878 A1 | 4/2012 |

\* cited by examiner

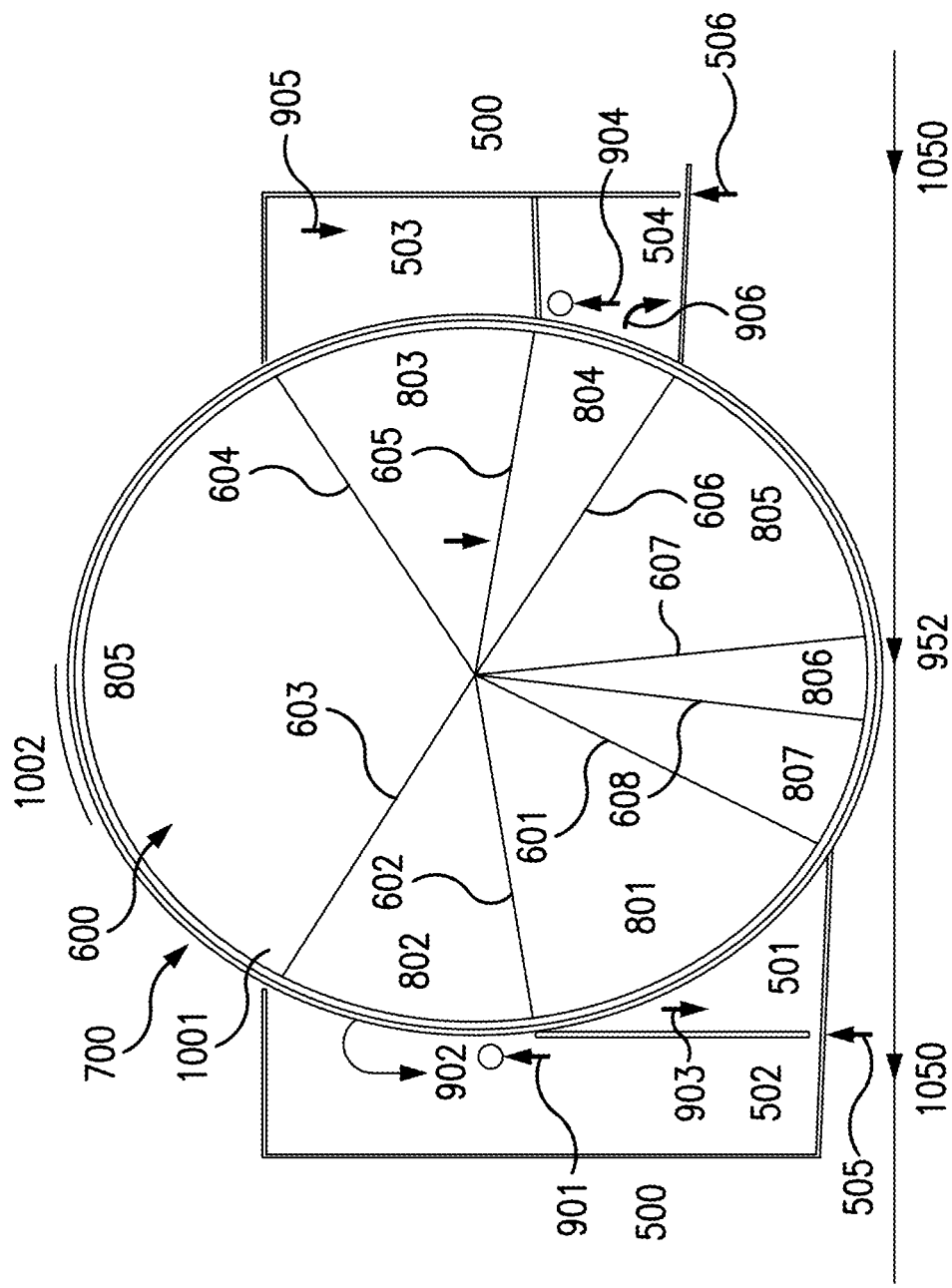

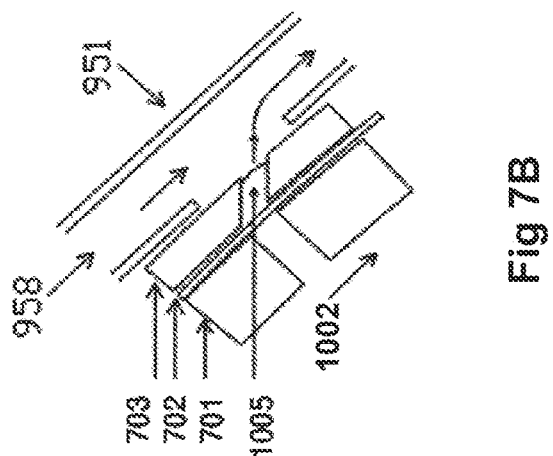
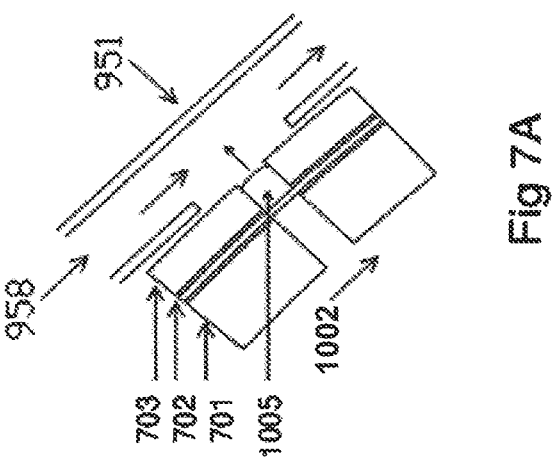
Fig 7

HIGH SPEED SAP PARTICLE APPLICATOR

FIELD OF THE INVENTION

The present invention relates to an apparatus and a method of applying single SAP (Super Absorbent Polymer) type granules or multiple SAP type granules at high speed in a predetermined continuous or intermittent profile onto a carrier layer or into an air stream, e.g. for use in the manufacture of an absorbent article, such as diapers for babies or adults, training pants, pull-up diapers (diaper pants), sanitary napkins, panty liners or the like. These articles typically comprise a carrier layer with the SAP particles and/or a mixed SAP and fiber core together with further layers, as may be combined with further elements for making up the complete article.

BACKGROUND OF THE INVENTION

The term "SAP" granules or particles as used herein interchangeably include materials capable of absorbing and storing a high amount of liquid compared with the volume thereof. "SAP" is the abbreviation of Super Absorbing polymer. In the present context, the SAP material may be used as granules of different particle size including powder like materials, fibers or a mixture of powder material and granules of different particle size or forms such as fibers.

SAP materials of this kind are usually embedded into absorbent pads of melt blown fibers or natural based fibers such as cellulose fibers (or similar fibrous materials and combinations thereof) or deposited onto a carrier layer such as of non-woven material. Absorbent article comprising such a core may be used for example for manufacturing a diaper, a sanitary towel or a liquid gathering article of any kind.

Various approaches have been proposed for obtaining SAP granule distribution having a predetermined pattern and/or local basis weight profile, such as in U.S. Pat. No. 5,156,902 (Pieper; K-C). These approaches include blowing an airborne mixture of SAP granules and fibers through a conduit onto a vacuum drum. Methods of this kind only allow a limited control of the pattern and the distribution of the local basis weight of the SAP over the area over which the SAP is distributed.

Particularly in case of low or no cellulose fiber containing absorbent cores, having SAP granules as the primary or even only liquid storage material, SAP granule distribution with accuracy with respect to shape and discreetness is highly important.

In this context it should be mentioned that it is possible to use single or multi piece cores, one layer of SAP or several layers on top of each other overlapping or besides each other. This also allows the use of different SAP in different layers. Thus the possibilities of variation of the achieved product are nearly endless. However, high accuracy of the granule distribution is important.

Achieving a profile of SAP within an absorbent article where different local basis weights of SAP can be applied at different points within the article is often desired as this allows SAP to be placed in locations where the SAP will be most useful. Within an absorbent article such as diaper for instance, applying a higher basis weight of SAP in the crotch region compared to the far ends (front and back) of the diaper typically achieves a better "in-use" utilization of the SAP.

Often, commercially available production equipment—including the one as described in the above references U.S. Pat. No. 5,156,902—uses a nozzle with an air feed (such as compressed air) to apply SAP into the production process. By default however, as the nozzle outlet is relatively small, the nozzle needs to be placed a significant distance away from the pulp/SAP blending process to allow the correct spray width in the SAP to be achieved prior to the subsequent combining with pulp. Placing the nozzle far away from the pulp/SAP blending process significantly reduces the performance of any pulsing device. At high speeds, even if a perfect pulse is created in the SAP stream at the entrance to the nozzle, by the time the pulse reaches the lay-down area much of the pulse has disappeared. This effect is partly due to turbulence within the equipment used to blend the pulp and SAP, but also as the particles of SAP do not have equal properties such as density variances in particle size (also known as particle size distribution), variances in air-resistance properties, particles exiting the jet gun typically follow a process similar to a particle spectrometer and/or aero-dynamic particle sizer (APS) where denser particles with less air resistance travel further than lighter particles with more air resistance. By designing the pulsing process to be of similar width as the laydown process allows the pulsing unit to be positioned significantly closer to the laydown process thereby ensuring that the pulse losses within the equipment are significantly reduced.

By utilizing a rotatory SAP pick and place device where defined amounts of SAP can be metered into a transfer or pick and place drum at defined locations allows a very accurate pattern of the SAP particles, see especially U.S. Pat. No. 7,838,722 or EP1621166 or WO2012/48878. This SAP printing, however, is quite inflexible with regard to changes in the pattern design.

Furthermore, such systems do not allow the use of multiple types of SAP particles or only with significant complications. Such a system for distributing different types of SAP in different regions of the absorbent article would have significant cost and environmental benefits. If for instance SAP of type "A" would be added to the crotch area of a diaper and SAP of type "B" to the ends of the diaper, SAP A could be fine-tuned to perform in it's specific application area, which may include faster permeability, and SAP B could be fine-tuned to perform in it's specific application area, which may include slower permeability. Furthermore such a device would open up the option to use lower cost SAP types in areas of the diaper where a high performance SAP was not required.

It would further be desirable to link a pulsing device with conventional pulp/SAP blending processes that does not cause secondary process issues in the core laydown process, as pulsing airflows are not desired in any pulp/SAP blending process.

Thus the present invention aims at providing a solution to the above problems by designing the device allowing to have a continuous air stream despite the SAP being pulsed therein, thusly providing a more stable subsequent pulp/SAP blending or lay-down process to be achieved. By varying the profile characteristics of the metering drum or roll, the pulse can be accurately tuned to deliver an exact pulse, albeit at a significant change part effort Furthermore, such a system could also be "fine-tuned" to compensate for pulse variations which take place between the SAP outlet and the pulp/SAP blending process.

Further a pulsing device described herein essentially has the capability not only to deposit SAP into an air stream for subsequent pulp and SAP blending but can also be used to deposit SAP directly onto a substrate. Such a device could therefore be installed on existing hygienic production systems producing a conventional pulp/SAP core and, should the hygienic producer wish to modify production process at a later date to produce SAP only cores, the equipment could be re-used with little modification.

Further process enhancements to this apparatus and methodology are to feed the SAP into the print roll via a SAP cascade system versus fluidized bed. The fluidized bed apparatus and methodology, although functional is has some process disadvantages in that (i) the secondary fluidized bed disturbs SAP pre-filled holes on the print-roll leading to cross contamination of SAP and also reduces the metering accuracy of the process (ii) the fluidized bed actually segregates the SAP particles causing an un-even particle size distribution, (iii) requires energy, (iv) creates exhaust air that exits the system that has to be managed via the linking to air filtration systems, (v) does not fully fluidize the SAP across the entire surface of SAP coming in contact with the print-roll thereby slightly damaged the surface of the SAP that comes into contact with the print-roll.

SUMMARY OF THE INVENTION

In a first aspect, the present invention is an apparatus for applying single or multiple types of SAP granules to an absorbent structure, the apparatus comprising A—a transfer device, preferably a rotatable drum, comprising A1—an essentially static stator defining a rotational axis along a width (y-)direction and a radial (r-)direction away from the axis;

A2—an outer revolving drum positioned relative to the stator such that it may rotate around the stator and comprising holes in a predetermined pattern, which extend essentially (r-) directionally throughout the thickness of the drum;

A3—an inner revolving drum positioned between the outer revolving drum and the stator comprising channels penetrating there through;

A4—a screen positioned between the inner revolving drum and the outer shell revolving drum, optionally connected to said holes of said outer drum or rotatably mounted wherein the screen comprises apertures adapted to the particle size of the SAP and preventing at least 95% of the SAP granules to not penetrate there through.

The apparatus further comprises at least one SAP granule supply system, operating as a fluidized bed or SAP cascade system that creates a cascade of SAP which falls over the revolving drum (SAP print roll) similar to a "water-fall" which is adapted to provide SAP particles to the holes of the outer revolving drum, and (C)—an air vacuum and pressurizing system connected to the stator as well as (D)—a SAP granule receiving system, preferably selected from the group consisting of an air duct and an air permeable carrier web.

The stator of the apparatus comprises a multiplicity of circumferentially arranged rings and dividers forming stator chambers, the chambers being arranged to be selectively connected to the vacuum and pressurizing system. At least one channel of the inner revolving drum exhibits an orientation deviating from the r-direction. Further, the holes of the outer drum are selectively connected via the holes of the inner drum to the chambers of the stator.

In a second aspect, the present invention relates to a method for applying singular or multiple types of SAP granules into a SAP granule receiving system, preferably selected from the group consisting of an air duct and a carrier web, the method comprising the following steps:
a) Providing an apparatus as described in the above;
b) Providing at least a first plurality of SAP granules;
c) Positioning a hole of the outer drum in the proximity of the at least first plurality of SAP granules;
d) Providing a vacuum in predetermined vacuum chamber of the stator;
e) Positioning a first channel of the inner drum such that it connects the hole in the outer drum with the vacuum chamber in the stator,
   such that SAP granules are positioned into the holes of the outer drum,
   the positioning being supported by the vacuum,
   and such the SAP granules are retained in the holes at at least 95% by the rotating screen;
f) Rotating the outer drum at a predetermined angle;
g) Expelling the SAP granules from the hole to the SAP granule receiving system, preferably by connecting the hole in the outer drum to a pressure chamber in the stator by a second channel in the inner drum.

Preferably, though not necessarily, the holes of the outer drum have a cylindrical shape with a radially oriented axis, though for example inclined axes, holes tapering towards the inner surface, or non-circular cross-sections may be employed, too. On its outer periphery, the outer drum may have holes of a size of at least 1 mm$^2$. The holes may form a pattern that may form arrays of holes separated by non-apertured regions.

In course of a filling step, different holes may be connected to different chambers such that, for example, one hole may be connected to a vacuum chamber whilst another one may be connected to a pressurized air chamber, leaving this hole empty for being filled in a subsequent filling step.

In a particular execution of the present invention, the SAP granule receiving system comprises a carrier web as a non-woven carrier web with at least one of a support roll, and a moving belt, and optionally travelling at a carrier speed of at least 20 m/min, or even at least 100 m/min, onto which the granules are positioned by a positive air pressure applied to the holes or by gravity. The expelled SAP particles may form a pattern on this carrier, which may reflect the pattern of the holes of the holes of the outer drum. Optionally a cover web may be positioned on the carrier and the SAP granules.

In another particular execution of the present invention the receiving system comprises an air duct, into which the SAP granules are fed. The air duct may comprise an air stream which may be loaded with other particles, such as—without any limitation—fibrous material, such as cellulosic fibers.

Optionally, the air duct has a width larger than the largest y-directional extension of the pattern of the holes of the outer drum.

The apparatus according to the present invention may further comprise an immobilization system, such as an adhesive or glue applicator, preferably of the hot melt applicator type, that may apply glue before, during or after the SAP granules are transferred to the SAP receiving system.

Optionally, the vacuum as applied to the chambers of the stator that are connected to the holes whilst these are filled with SAP granules may be adapted by a control mechanism comprising a loss-in-weight system of the SAP granule supply system. Optionally, the apparatus may comprise a scarfing system such as a doctor blade positioned at a predetermined distance from the outer surface of the outer drum, wherein this distance may be adjusted according to a loss-in-weight system of the SAP granule supply.

The method and the apparatus according to the present invention may be employed in the manufacture of absorbent cores for disposable absorbent articles, such as without limitation diapers for babies or adults, training pants, pull-pull on diapers sanitary napkins or panty liner, which may comprise other components such as liquid handling enhancing elements, such as liquid acquisition and distribution material, optionally comprising modified cellulosic fibers. An array of holes of the outer drum may correspond to each one core of such an absorbent article.

BRIEF DESCRIPTION OF DRAWINGS

FIG. 4A to F depict schematically various distribution pattern of SAP granules in an absorbent structure, such as may be useful in a hygienic product corresponding to a top view of a sheet blank of a drum.

FIG. 5 illustrates a process according to the present invention wherein two types of SAP granules are applied to a carrier material.

FIG. 7 depicts schematically two particular embodiments according to the present invention for applying SAP granules into an air stream FIG. 8 with an enlarged section B depicts a further detail according to the present invention.

Same numerals in various figures refer to same or equivalent features or elements.

DETAILED DESCRIPTION OF INVENTION

Figure 1A:
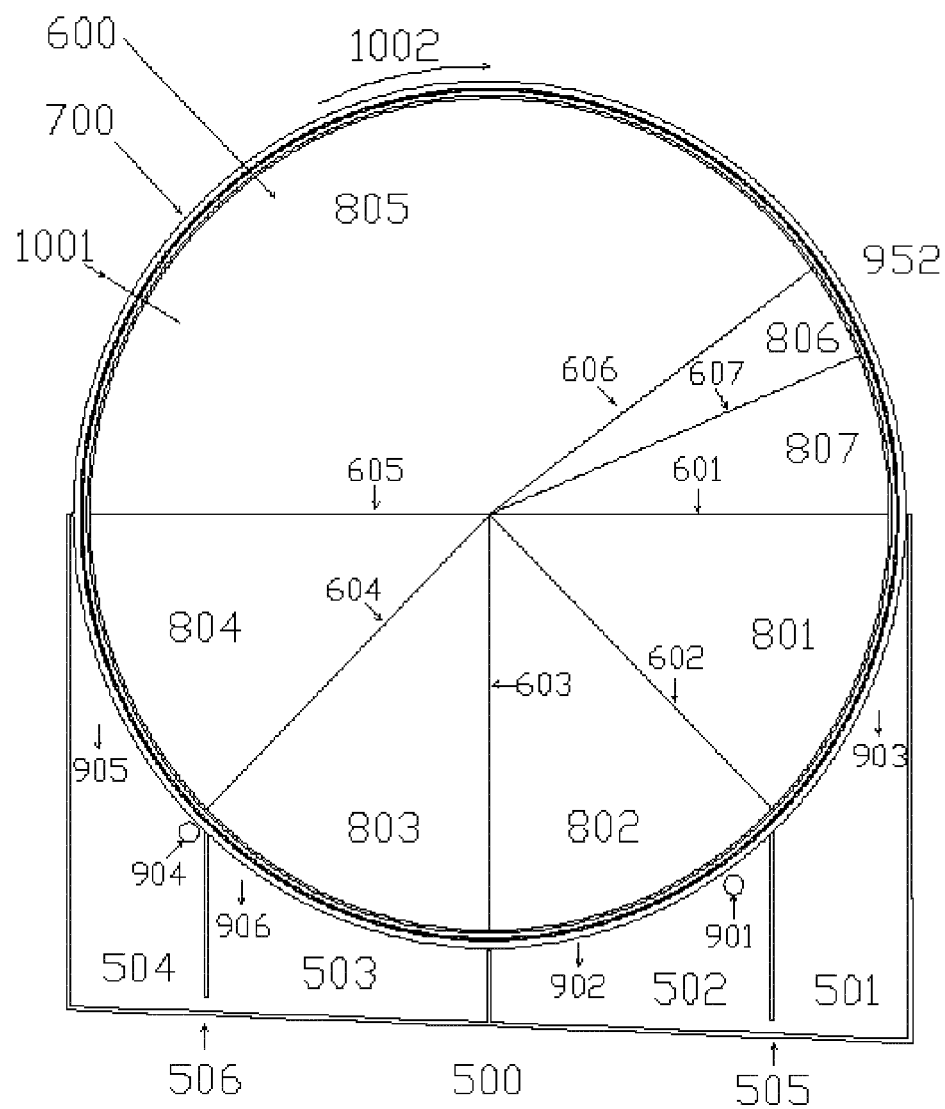
FIG. 1A to E schematically depict elements suitable for executing the present invention.

Thus the present invention is directed to an equipment and a method for applying one or more types of SAP particles or SAP granules as may be referred to interchangeably, into an air stream or onto a surface with high accuracy of the distribution (pattern), amount and composition of SAP material by a transfer device, as may be referred to interchangeably as pick and place device with the respective method using a rotating drum with holes. Such a process method may be used in an application of SAP particles requiring accurate, print like positioning of granules or particles on a carrier layer. One particular application may be the making of primarily SAP comprising cores for disposable diapers or parts of such cores, wherein the SAP is immobilized such as by glue.

According to a first aspect of the present invention, the transfer method according to the invention comprises the following process steps:

SAP granules are provided and positioned close to a rotating SAP transfer device. The granules are mobilized in a fluidized bed by injecting air into or vibrating the SAP or preferably SAP is applied via a cascade system that creates a cascade of SAP which falls over the revolving drum (SAP print roll) similar to a "water-fall" allowing SAP to gently be sucked into the holes. Alternatively, the granules by be brought in contact with the rotating device by other means, such as described in U.S. Pat. No. 7,838,722, to which express reference is made for this aspect.

The rotating SAP transfer device has a number of holes or apertures of a defined size and location, their respective location dictating where SAP will be held, and their size determine the volume and hence amount of SAP held.

The SAP transfer device is rotating through or close to the particle bed and/or cascade whilst air is blown or sucked through the holes. Holes having air blown from within the hole will by default not be able to pick up SAP whilst holes having a vacuum applied will suck SAP within the hole.

Whilst the SAP transfer device continues to rotate, the SAP granules inside said holes are hold by appropriate means, such as vacuum.

The rotating SAP transfer device to a first pattern definition area where a defined amount of SAP can be removed, such as by reducing the vacuum suction or blowing air outwardly through the holes. These steps may be repeated through additional SAP pick up stations that can be repeated between anywhere from 1 to 100 times.

The transfer device being rotatably moveable from the partial deposition area(s) to the SAP granule receiving system, e.g. a final particle release area where SAP particles can be applied onto a carrier layer (transfer or meeting position) or into an air stream, optionally supported by means for expelling said SAP granules.

According to another aspect the present invention refers to an apparatus.

In the following, the transfer or "pick and place" device shall mean the transfer of SAP, which is separated from the bulk storage of SAP before it is in contact with the receiving system, i.e. by not having a continuous stream of granules.

The present invention provides a method and apparatus that among other benefits significantly increases SAP deposition accuracy. The standard deviation achieved so far has been reduced to about ¼ of what has been achieved with advanced prior technology. For example diaper cores having an accurate distribution profile of SAP in the lateral and the longitudinal direction can be obtained. The method according to the invention allows especially deposition of SAP granules on fast moving carrier layers at surface speeds of 1 m/sec up to 3 m/sec, preferably up to 5 m/sec, or even 10 m/sec and even more preferably up to 15 m/sec with high accuracy. Because of the accuracy of the deposition of SAP granules, the invention allows manufacturing of e.g. an absorbent core without cellulose or similarly absorbent and/or hydrophilic fibers in diapers which results in extreme core thinness and improved comfort and fit in use for the articles.

The term "transfer device" or "pick and place device" as used herein includes any moveable member being capable of taking up SAP granules in a predetermined shape and a thickness profile and transferring the granules without significantly amending the configuration thereof to a SAP granule receiving system, such as a carrier substrate or into an air duct.

A preferred embodiment of the transfer device is a patterned rotary drum or roll, which is called "pick and place drum" or "transfer drum" in the present context because the transfer of a pattern of SAP granules can be comparable with a pick and place process. Another embodiment within the general scope of the present invention is a moveable belt having holes on the surface and being moved between the SAP granule bulk storage and the receiving system.

The term "bulk" or "bulk storage" of SAP granules refer in the present context to any kind of supply of granules, particularly a hopper.

"Retaining means" are provided to keep the SAP granules taken up by the holes of the transfer device in these holes during movement from the bulk to the transfer position where the granules are delivered to the carrier layer. In one preferred embodiment, the retaining means is a belt, which is guided along the surface of the transfer device, particularly the printing drum or roll, on the way from the bulk to the transfer position. Other possible embodiments, which are particularly preferred, are vacuum means for keeping the SAP granules in the holes. Also the use of an electrostatic field is possible.

"Expelling means" in the present context, means delivering the SAP granules in the transfer position as defined above to a carrier substrate. For delivering the granules, the granules may be expelled by air jets or an electrostatic field or just by gravity or inertia.

The above and further features, aspects and advantages of the present invention will become better understood with regard to the following description making reference to the accompanying drawings, which however should not be seem limiting the scope of the present invention.

FIG. 1A illustrates an overall layout of key elements of the present invention with a revolving SAP transfer drum (700) with holes where the drum can rotated both clockwise and anti-clockwise and in this example would rotate clockwise (1002). A static stator (600) can provide constant vacuum (negative pressure air compared to ambient conditions), varying vacuum or positive pressure air to the SAP pick and place drum (700). A hopper (500) contains SAP granules, optionally in a fluidized state, with a first chamber (501) of SAP granules, here shown as SAP granules of the type A and in a fluidized bed, and a first catchment tray (502) where SAP which is not transferred to the drum is caught, and via the gap in the wall between first chamber (501) and first catchment tray (502) can return to the first chamber (501), either by gravity or assisted by a recycling means (505). A second chamber of fluidized SAP (503), here shown with SAP granules of type B, and a second catchment tray (504) where SAP falling is caught, and via the gap in the wall between the second chamber (503) and second catchment tray (504), either by gravity or assisted by recycling means (506). The stator comprises a plurality of stator chambers formed by rings and dividers of the stator, which may be selectively connected to the vacuum source, and be referred to as dedicated vacuum chambers. A first dedicated vacuum zone (801) within the stator (600) can suck SAP particles from the first chamber (501) into the holes in the SAP pick and place drum or roll (700). A second dedicted vacuum zone (802) within the stator (600) can supply vacuum to the holes in the SAP pick and place drum (700) to allow them to be transported where a scarfing process may take place (901) and/or, the vacuum level in the second dedicated vacuum zone (802) would vary to allow SAP to fall away from the holes in the SAP pick and place drum (700). A third dedicated vacuum zone (803) within the stator (600) can suck SAP particles from (803) into the holes in the SAP pick and place drum (700). And a fourth dedicated vacuum zone (804) within the stator (600) can supply vacuum to the holes in the SAP pick and place drum (700) to allow them to be transported where a scarfing process may take place (904) and/or, the vacuum level in (804) would vary to allow SAP to fall away from the holes in the SAP pick and place drum (700). A further dedicated vacuum zone (805) within the stator (600) can provide vacuum to the holes in the pick and place drum (700) to allow them to transport granules to a discharge area of a receiving system. A further vacuum zone (806) represents a dedicated vacuum zone within the stator (600) which typically would supply air to the holes in the SAP pick and place drum (700) to allow them to be discharged at a discharge area (952). The system may further comprise secondary cleaning area (807) and also a screen and hole inspection system if required.

Figure 1B:
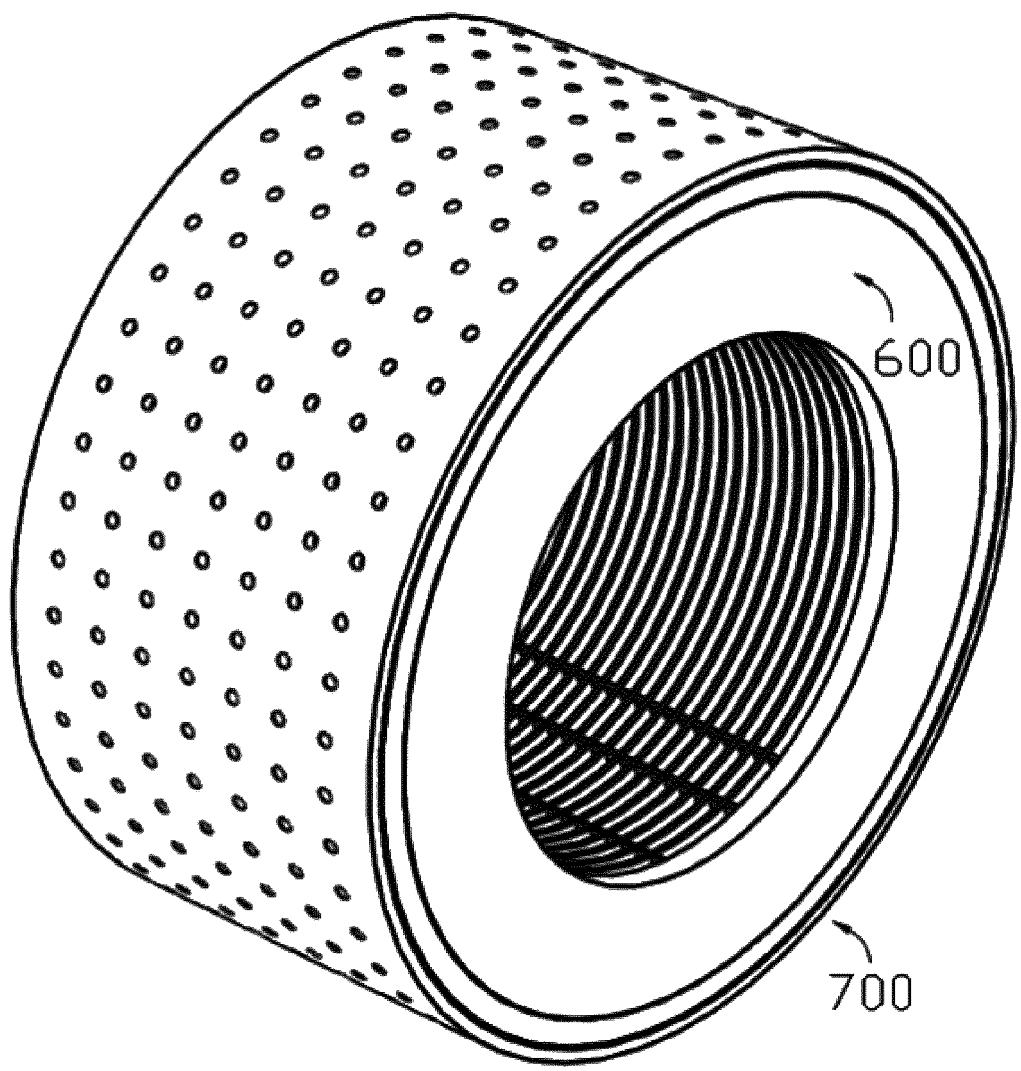

FIG. 1B is a 3-dimensional diagrammatic illustration of the revolving SAP pick and place drum (700) assuming a 2 up design and vacuum stator assembly (600) which remains static.

Figure 1C:
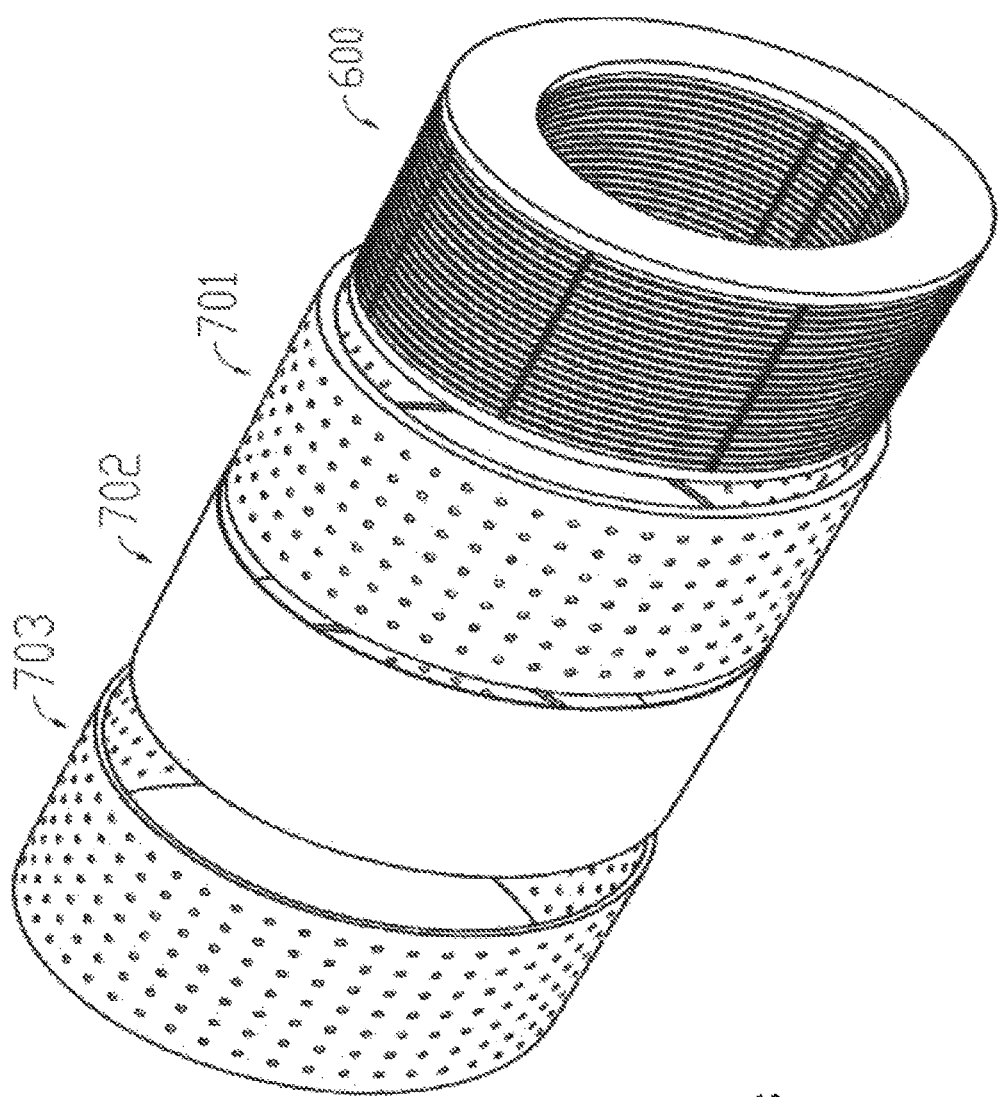

FIG. 1C is a 3-dimensional diagrammatic illustration of an exploded view of the SAP pick and place drum showing the inner revolving drum (701), the sandwiched rotating porous screen (702), the outer revolving drum (703) and vacuum stator assembly (600).

Figure 1D:
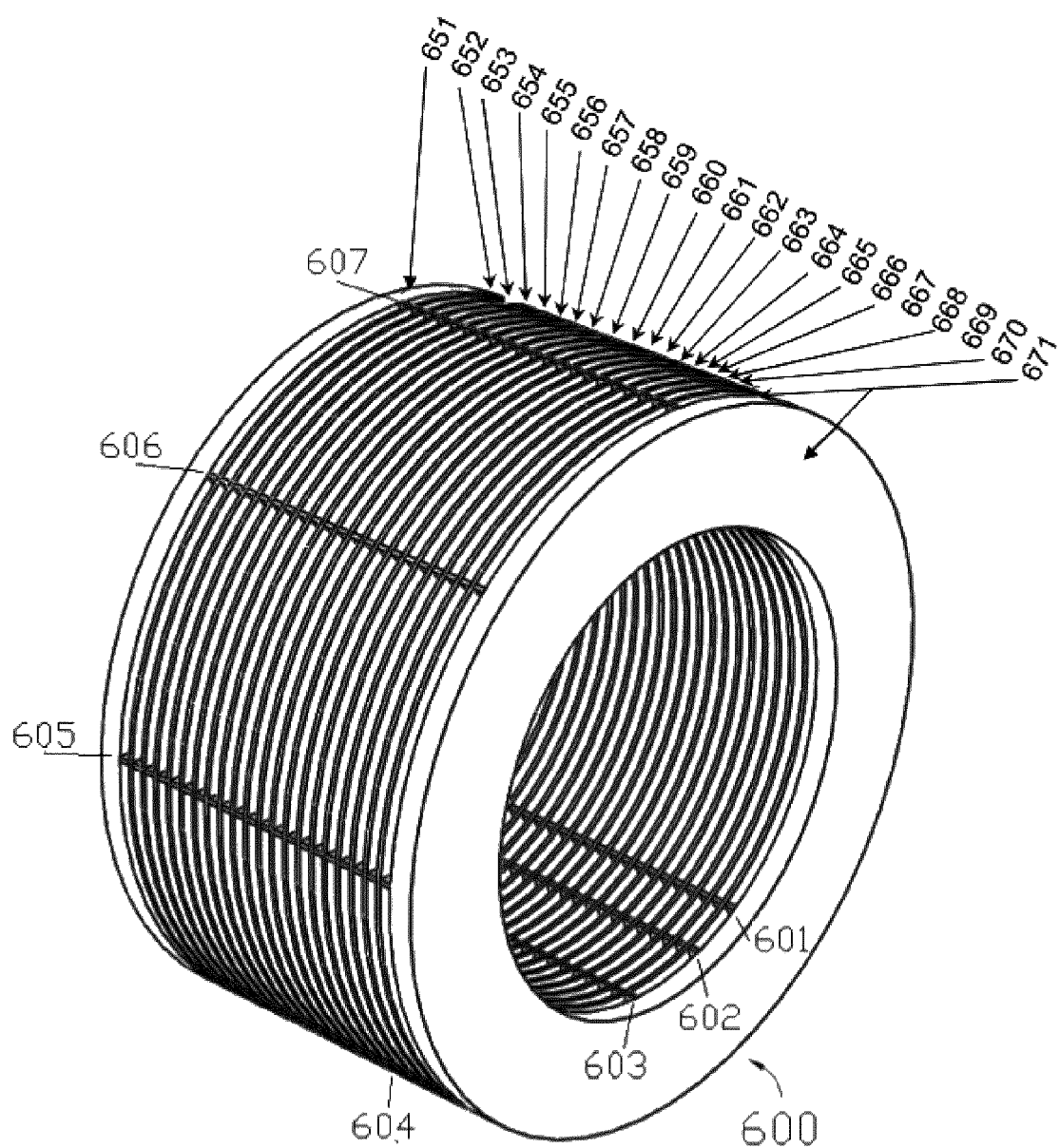

FIG. 1D is a 3-dimensional diagrammatic illustration of the vacuum stator assembly (600) showing the multitude of rings, (651-671) and dividers within the rings 601-607.

Figure 1E:
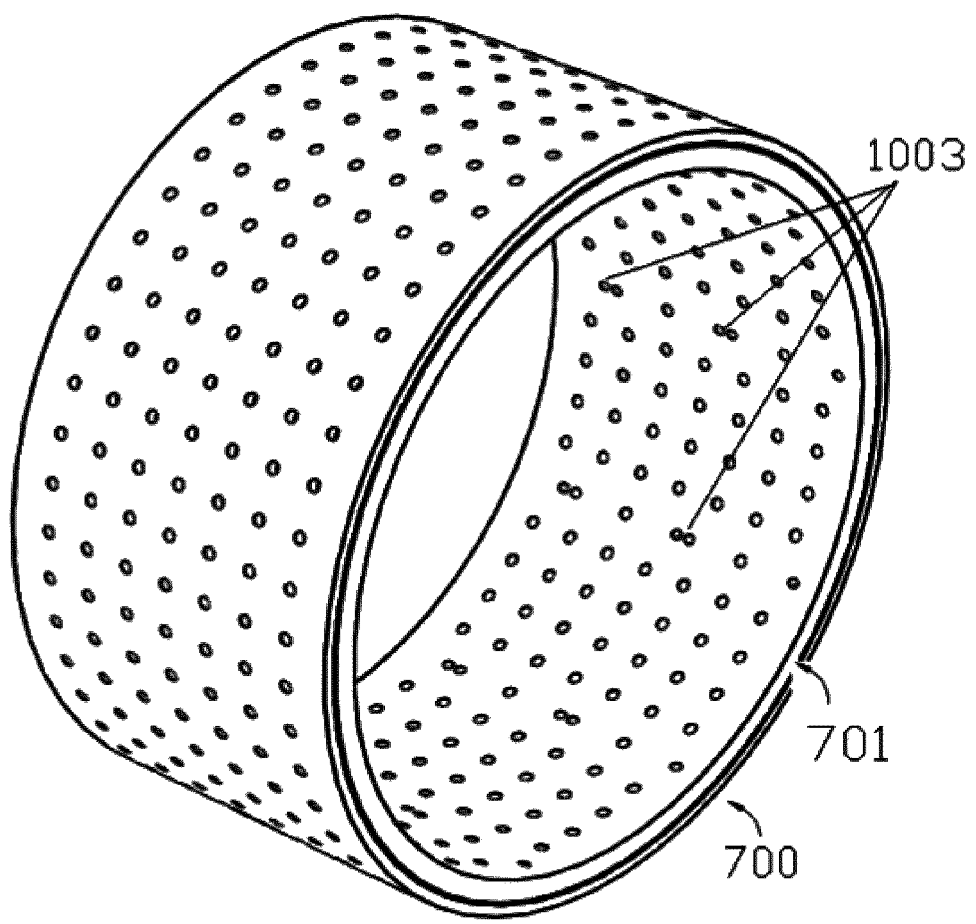
Figure 2A:
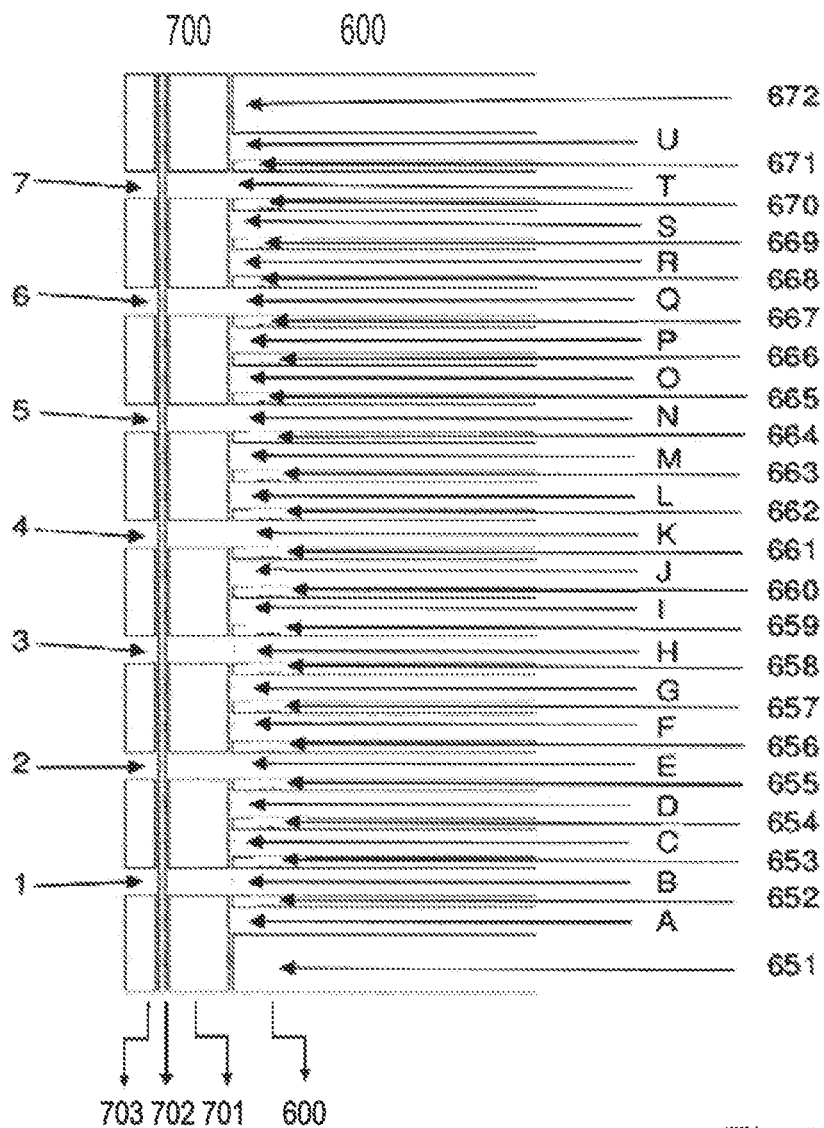
FIG. 2A to D show schematically various executions for equipment according to the present invention.

FIG. 1E is a 3-dimensional diagrammatic illustration of the SAP pick and place drum (700) showing a variety of hole locations (1003) on the inner revolving drum (701), FIG. 2A illustrates a two-dimensional diagrammatic illustration of the SAP pick and place drum that is shown in FIG. 1 as a cross sectional view of SAP pick and place drum (700) along line (1001) which shows the total build-up of the SAP pick and place drum with a certain design on the inner drum to allow access to specific vacuum areas in the vacuum stator (600), in this design, hole (1), is connected to vacuum chamber (B), hole (2) is connected to vacuum chamber (E), hole (3) is connected to vacuum chamber (H), hole (4) is connected to vacuum chamber (K), hole (5) is connected to vacuum chamber (M), hole (6) is connected to vacuum chamber (P), hole (7) is connected to vacuum chamber (S).

Figure 2B:
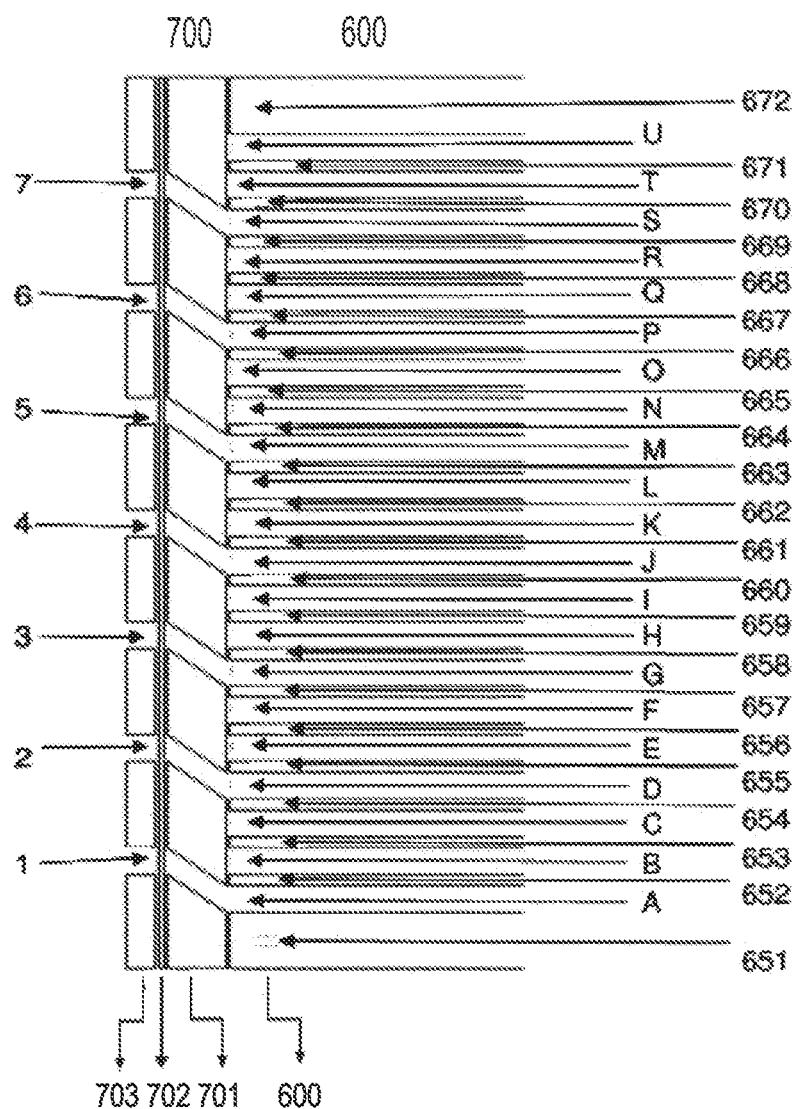

FIG. 2B illustrates a two-dimensional diagrammatic illustration of the SAP pick and place drum that is shown in FIG. 1 as cross sectional view of SAP pick and place drum (700) along line (1001) which shows the total build-up of the SAP pick and place drum with a certain design on the inner drum to allow access to specific vacuum areas in the vacuum stator (600), in this design, hole (1), is connected to vacuum chamber (A), hole (2) is connected to vacuum chamber (D), hole (3) is connected to vacuum chamber (G), hole (4) is connected to vacuum chamber (J), hole (5) is connected to vacuum chamber (M), hole (6) is connected to vacuum chamber (P), hole (7) is connected to vacuum chamber (S).

Figure 2C:
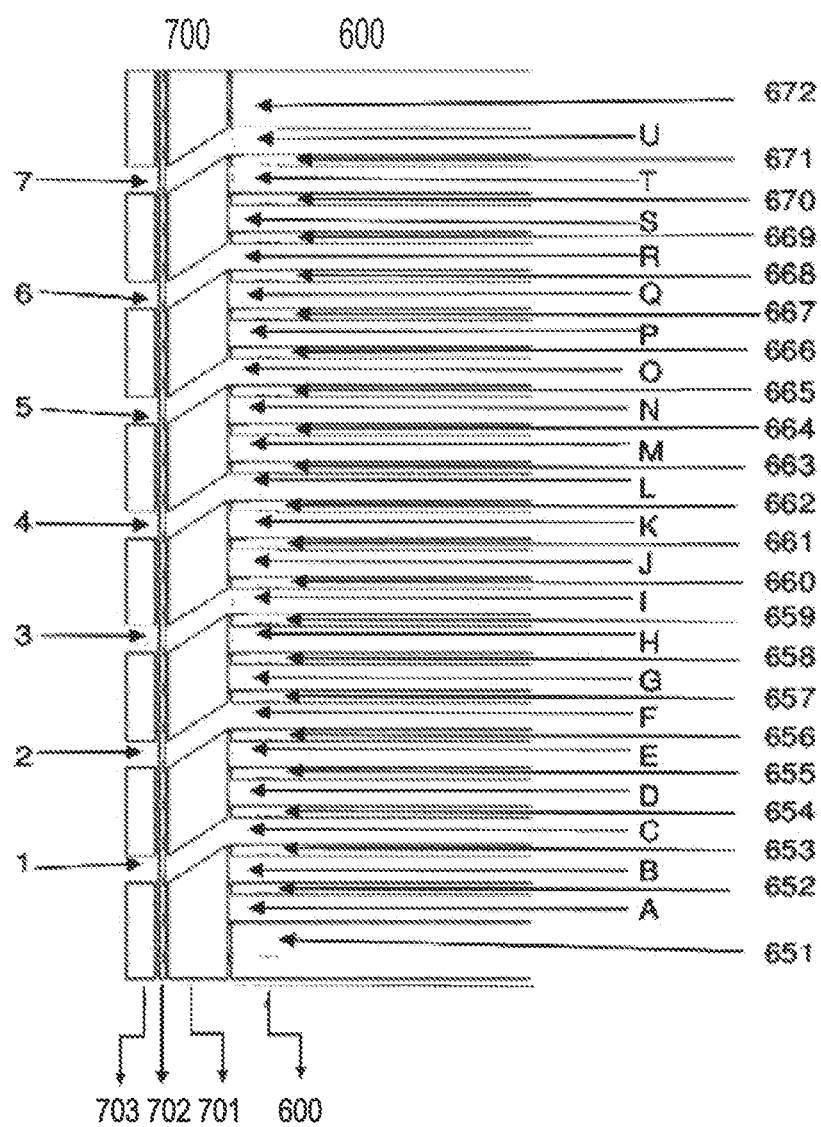

FIG. 2C illustrates a 2-dimensional diagrammatic illustration of the SAP pick and place drum that is shown in FIG. 1 as cross sectional view of SAP pick and place drum (700) along line (1001) which shows the total build-up of the SAP pick and place drum with a certain design on the inner drum to allow access to specific vacuum areas in the vacuum stator (600), in this design, hole (1), is connected to vacuum chamber (A), hole (2) is connected to vacuum chamber (D), hole (3) is connected to vacuum chamber (G), hole (4) is connected to vacuum chamber (J), hole (5) is connected to vacuum chamber (M), hole (6) is connected to vacuum chamber (P), hole (7) is connected to vacuum chamber (S).

Figure 2D:
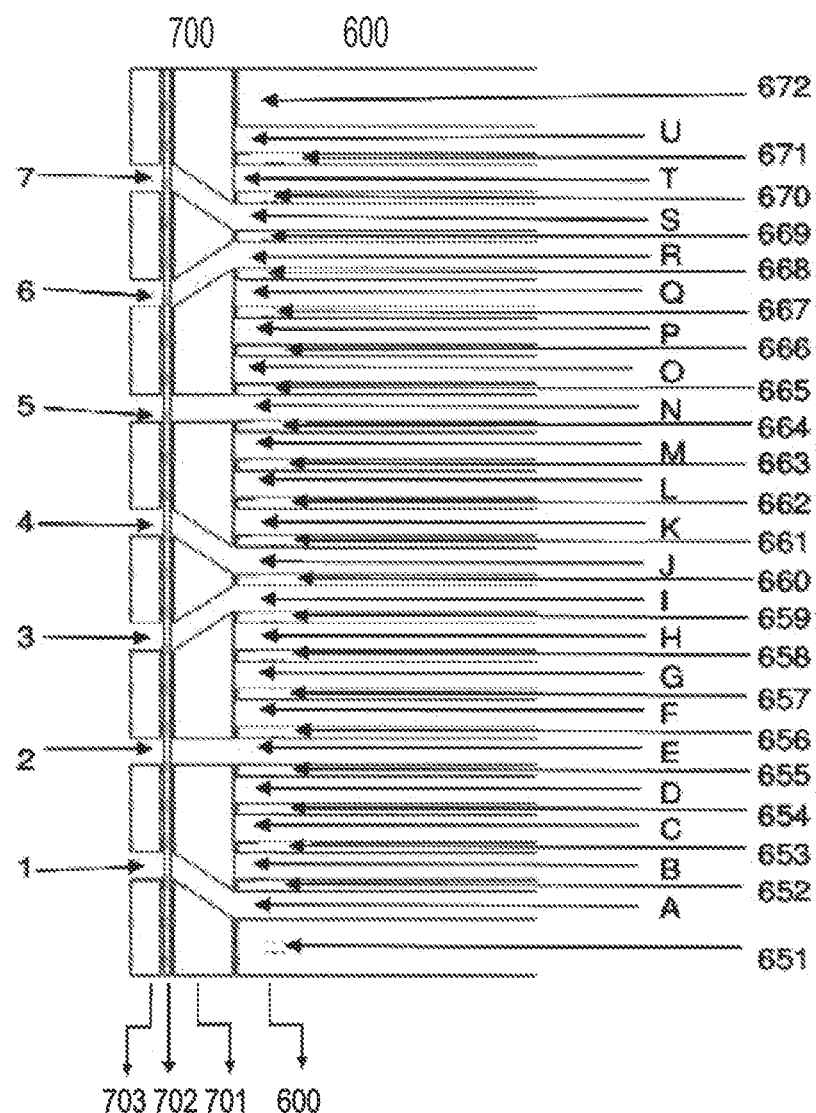

FIG. 2D illustrates a 2-dimensional diagrammatic illustration of the SAP pick and place drum that is shown in FIG. 1 as cross sectional view of SAP pick and place drum (700) along line (1001) which shows the total build-up of the SAP pick and place drum with a certain design on the inner drum to allow access to specific vacuum areas in the vacuum stator (600) in this design, hole (1), is connected to vacuum chamber (A), hole (2) is connected to vacuum chamber (D), hole (3) is connected to vacuum chamber (G), hole (4) is connected to vacuum chamber (J), hole (5) is connected to vacuum chamber (M), hole (6) is connected to vacuum chamber (P), hole (7) is connected to vacuum chamber (S).

Figure 3:
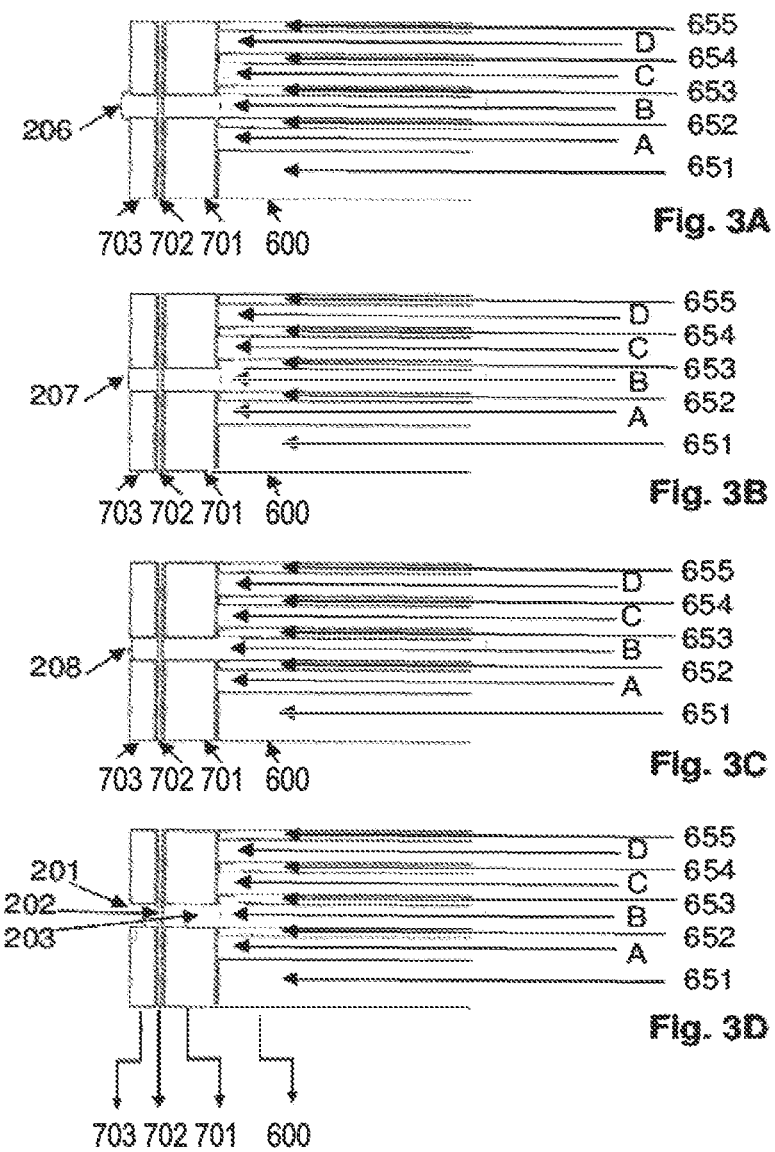
FIG. 3A to 3D illustrates various operation modes in the process according to the present invention.

FIG. 3 illustrates a 2-dimensional diagrammatic illustration of the SAP pick and place drum that is shown in FIG. 1 (cross sectional view of SAP pick and place drum (700) along line (1001) which shows the total build-up of the SAP pick and place drum with the following:

FIG. 3A represents a scenario where no SAP is present in the hole of the SAP pick and place drum (700) due to very low levels of vacuum (or positive air pressure) in the vacuum stator (600) sector B.

FIG. 3B represents a scenario where no SAP is present in the hole of the SAP pick and place drum (700) due to low levels of vacuum pressure in the vacuum stator (600) sector B.

FIG. 3C represents a scenario where no SAP is present in the hole of the SAP pick and place drum (700) due to mid-levels of vacuum pressure in the vacuum stator (600) sector B.

FIG. 3D represents a scenario where no SAP is present in the hole of the SAP pick and place drum (700) due to high levels of vacuum pressure in the vacuum stator (600) sector B.

Figure 4A:
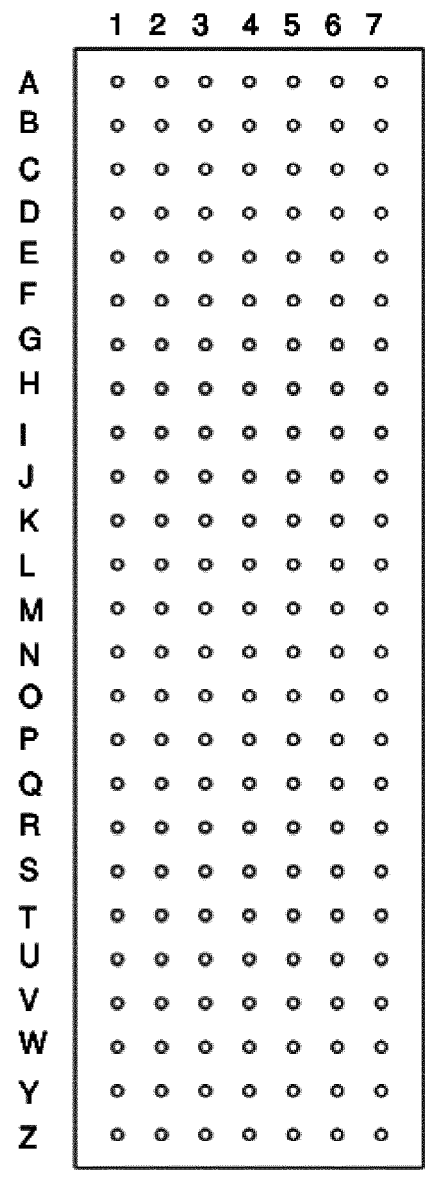

FIG. 4A illustrates a 2-dimensional diagrammatic illustration of an example hygienic product (1 up) which shows the possible place points of SAP onto the hygienic product with matrix descriptions in X and Y which will be used through this patent description where the marked holes in this patent description and also depicts a likely scenario where holes should have positive pressure applied when holes are being emptied of SAP.

Figure 4B:
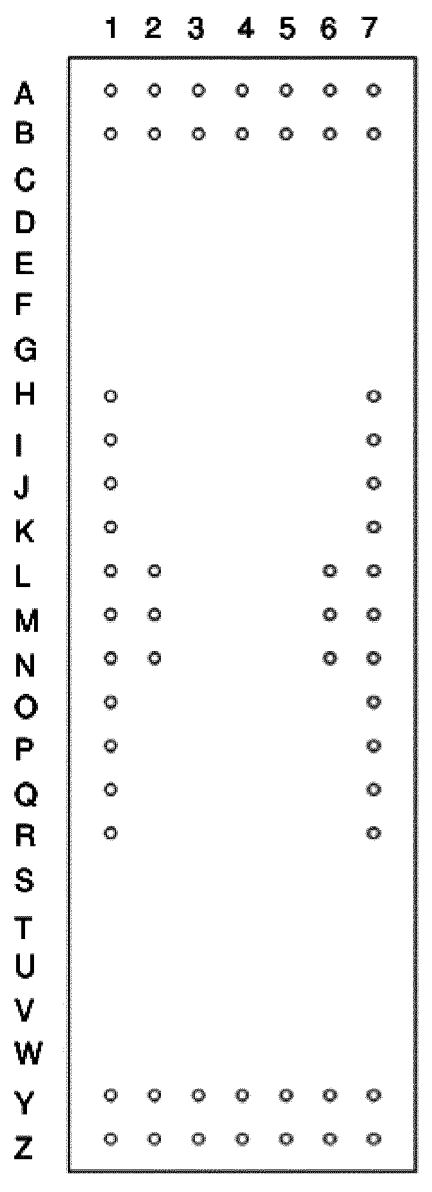

FIG. 4B illustrates a 2-dimensional diagrammatic illustration extending on FIG. 4A where the marked holes in this patent description could be locations where no SAP is required.

Figure 4C:
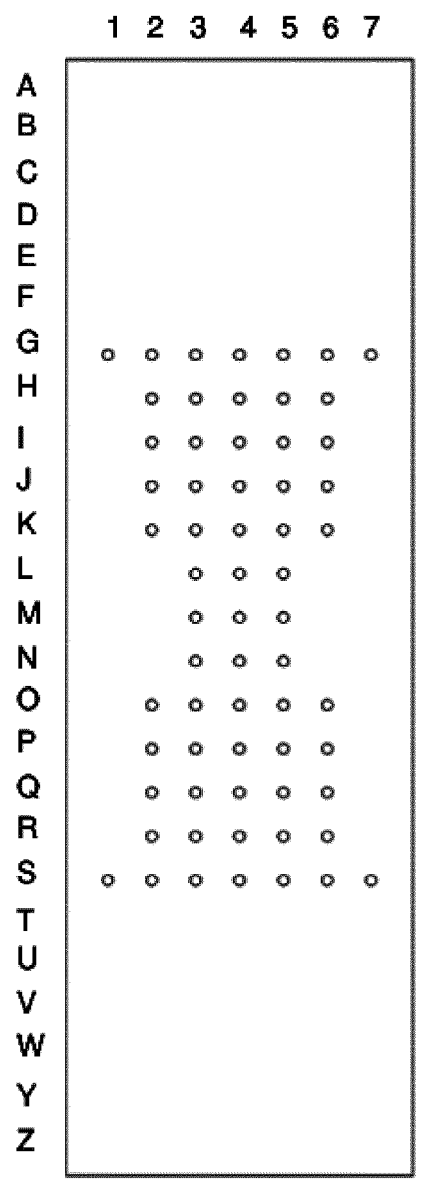

FIG. 4C illustrates a 2-dimensional diagrammatic illustration extending on FIG. 4A where the marked holes in this patent description could be locations where SAP type A is required.

Figure 4D:
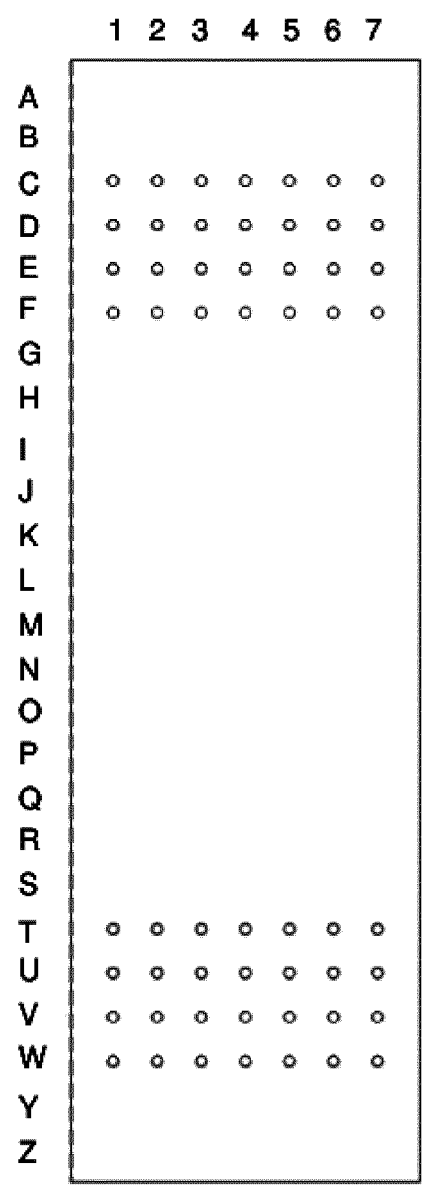

FIG. 4D illustrates a 2-dimensional diagrammatic illustration extending on FIG. 4A where the marked holes in this patent description could be locations where SAP type B is required.

Figure 4E:
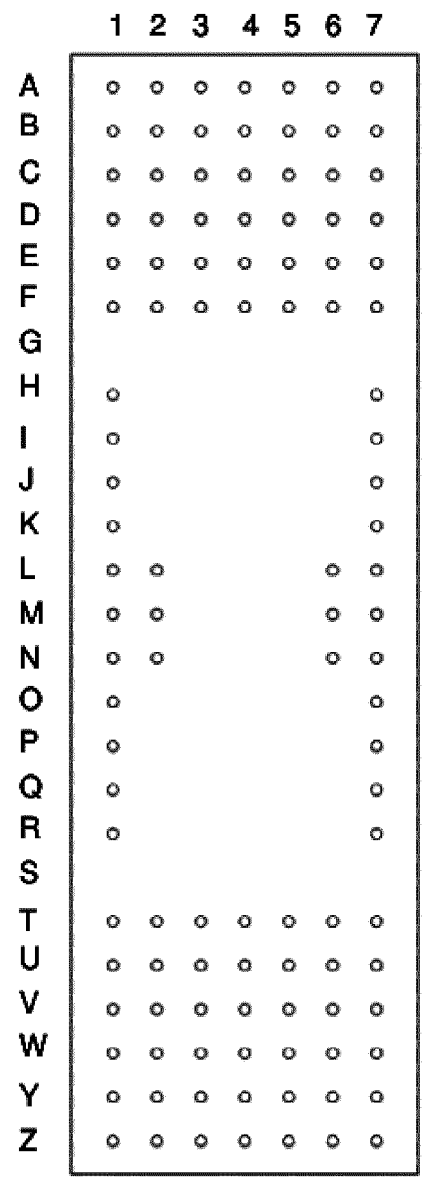

FIG. 4E illustrates a 2-dimensional diagrammatic illustration extending on FIG. 4A where the marked holes in this patent description could be locations where air is being blown when SAP type A is being filled.

Figure 4F:
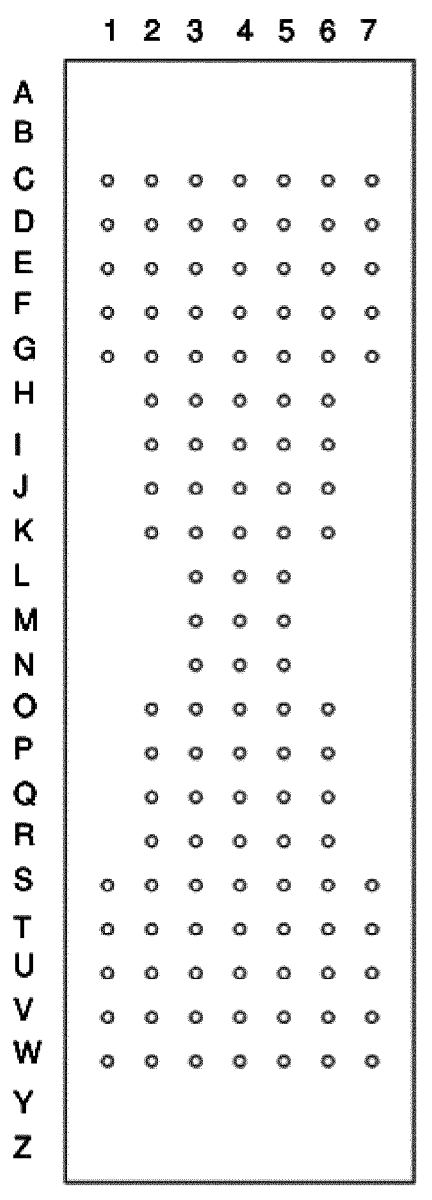

FIG. 4F illustrates a 2D diagrammatic illustration extending on FIG. 4A where the marked holes in this patent description could be locations where SAP is located after both filling processes have taken place.

FIG. 5 illustrates a process where SAP granules are being applied to a carrier web (952), such as a nonwoven material or a tissue substrate, which is moving in direction (1050). A revolving SAP granules pick and place drum (700) with holes can rotate both clockwise and anti-clockwise and in this example would rotate clockwise (1002). A static stator (600) can apply vacuum or positive air to the SAP pick and place drum (700). A hopper (500) contains fluidized SAP granules with a first chamber (501) of fluidized SAP where the SAP here is called SAP type A, a first catchment tray (502) where SAP falling is caught, and via the gap in the wall between first chamber (501) and first catchment tray (502) can return to the first chamber (501), either by gravity or assisted by recycling means (505). A second chamber (503) with SAP granules of the SAP type B, here shown in a fluidized bed arrangement, and a second catchment tray (504) where SAP falling is caught, and via the gap in the wall between second chamber (503) and second catchment tray (504), either by gravity or assisted by recycling means (506). The stator comprises a plurality of stator chambers formed by rings and dividers of the stator, which may be selectively connected to the vacuum source, and be referred to as dedicated vacuum chambers. A first vacuum chamber (801) represents a dedicated vacuum zone within the stator (600) which may suck SAP particles from first chamber (501) into the holes in the SAP pick and place drum (700). A second dedicated vacuum zone (802) within the stator (600) can supply vacuum to the holes in the SAP pick and place drum (700) to allow them to be transported where a scarfing process may take place at (901). Optionally the vacuum level in the first dedicated vacuum zone (802) can vary to allow SAP to fall away from the holes in the SAP pick and place drum (700). A further dedicated vacuum zone (803) within the stator (600) may suck SAP particles from (803) into the holes in the SAP pick and place drum (700). A further dedicated vacuum zone (804) within the stator (600) may supply vacuum to the holes in the SAP pick and place drum (700) to allow them to be transported where a scarfing process may take place at (904) and/or, the vacuum level in this vacuum chamber (804) would vary to allow SAP to fall away from the holes in the SAP pick and place drum (700). Yet a further dedicated vacuum zone (805) within the stator (600) may supply vacuum to the holes in the pick and place drum (700) to allow them to be transported to a discharge area and the receiving system. An even further dedicated vacuum zone (806) within the stator (600) which typically would supply air to the holes in the SAP pick and place drum (700) to allow them to be discharged at the discharge area (952) and the receiving system. A secondary cleaning area (807) and also a screen and hole inspection system (not shown) may be included.

Figure 6:
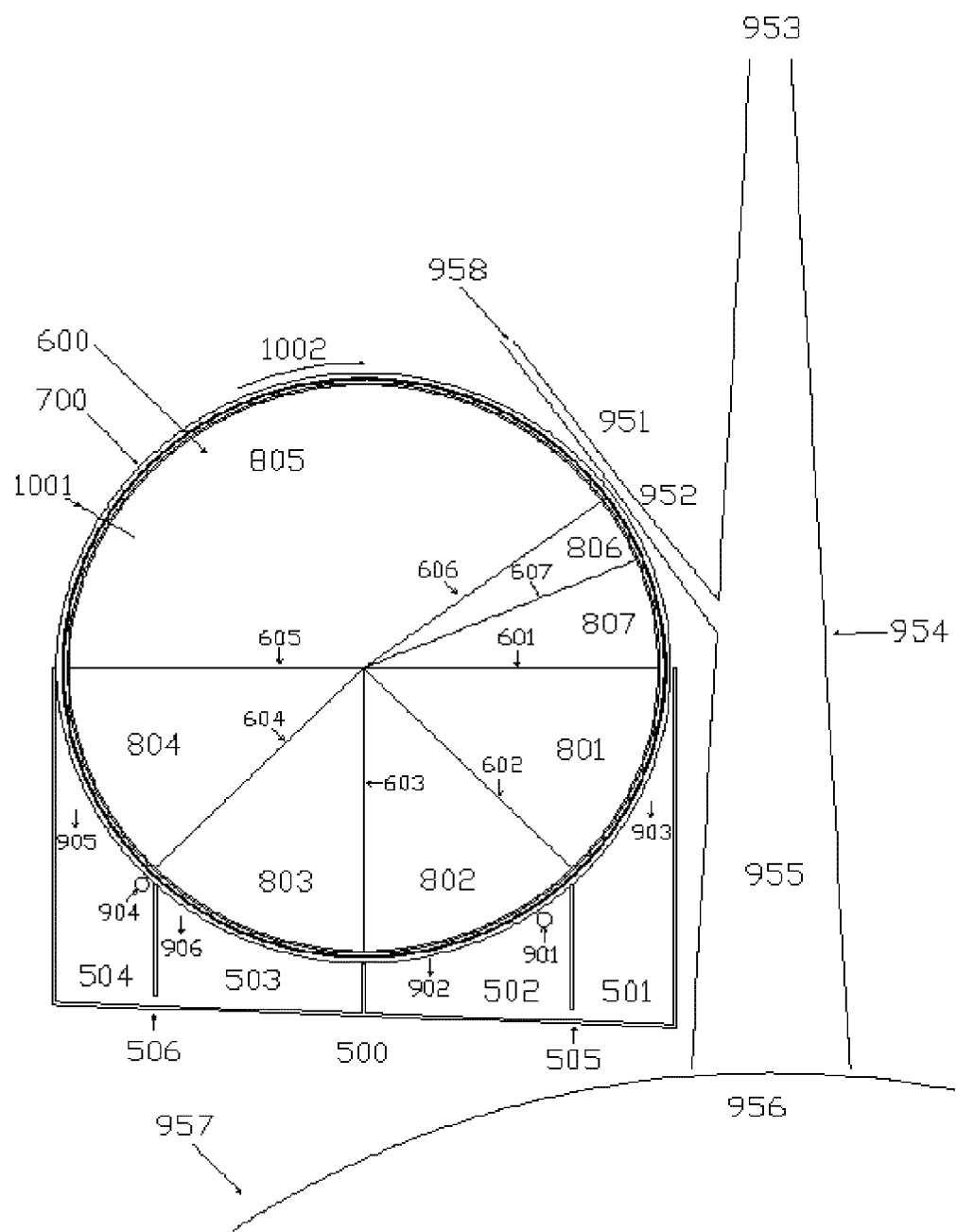
FIG. 6 illustrates an overall layout of the present invention connected to process where SAP is being applied to an air stream.
Figure 8B:
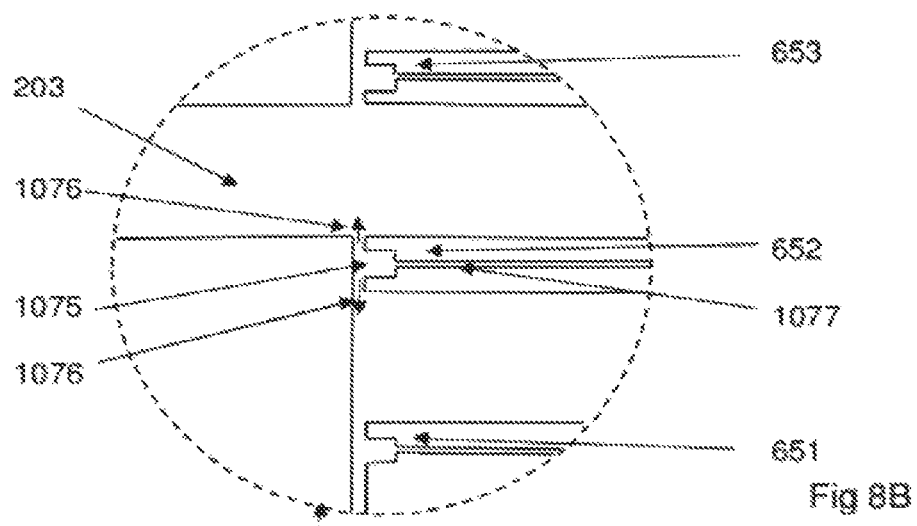
Figure 8A:
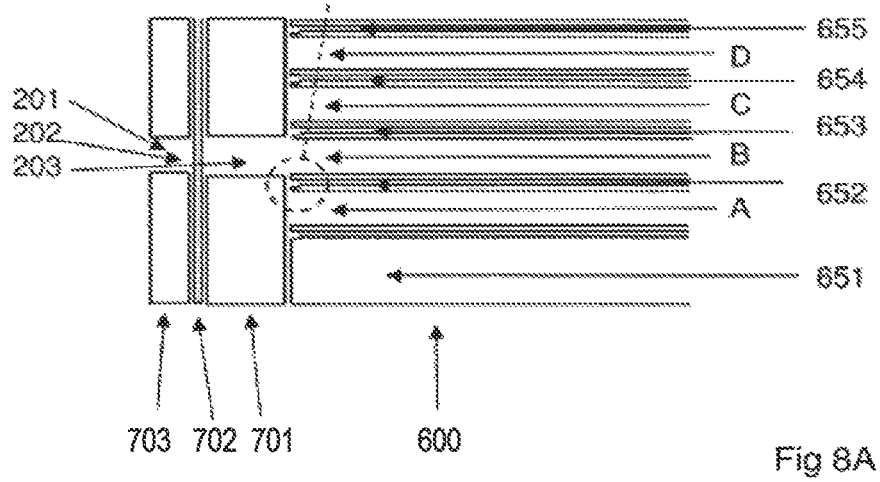

FIG. 6 illustrates an overall layout of the present invention connected to process where SAP granules are applied to an air stream (958) in a cavity (951) at an injection point (952). Other particulate material, such as pulp fibers, may be introduced at inlet (953) and transported in a cavity (954) to the blending region or area (955), where SAP granules and fibers are blended to be then laid down a laydown region (956) of a laydown drum (957).

FIG. 7 illustrates a modification in the stator which applied compressed air between the stator (600) and pick and place drum (700) where FIG. 7A shows a first scenario where the angle of the holes in the outer drum (703) is at 90 degrees to direction of motion, and where FIG. 7B shows a second scenario where the angle of the holes in the outer drum (703) is at 135 degrees to direction of motion thereby increasing SAP speed into the chute (951) in the direction if moving air (958).

FIG. 8 illustrates a scenario where air in injected within vacuum stator (600) into cavity shown as (1075) in washer (652) thereby creating an airflow (1076) preventing dust particles from being trapped between (600) and (700) and causing excessive machine wear.

The pick and place SAP drum (700) with holes in outer component (703) rotates past filling and emptying stations where SAP is deposited within the holes. Due to the high rotational speed of (700), centrifugal forces can reduce SAP fill rate, or, even in some instances prevent the holes from filling with SAP and as such, vacuum assistance is required which is supplied from the vacuum stator (600) which remains stationary. To transfer the air into the holes in the outer component (703) a porous screen is used (702) which is kept in place by (701) and (702).

For volumetric dosing where a specific volume of SAP is required, the holes are simply filled and then passed onto a subsequent deposition process where the holes are emptied.

For gravimetric dosing, the volume of SAP feed varies to keep the average granules flow constant. This is required as the relative density of the SAP can change. In such a process, data from a loss and weight process is used to adjust the volume of SAP being removed by the pick and place SAP drum (700). In such a process, SAP is being fed into pick up zones (501) and (503) at a controlled rate, as may be adjusted by a loss in weight feeding process. Sensor in the pick up zones (501) and (503) depicted as (903) and (905) detect SAP quantities in the pick-up zones and adjust take away volumes accordingly.

Take away volumes are either adjusted by varying the vacuum levels in (802) and (804) the effect of which is documented in FIG. 3, or by using a scarfing concept which could be an air knife, scraper, or rotating device. In these embodiments, the air knife airflow can be adjusted to change the volume of SAP being transported in the holes, or, the height of this system above (703) can be adjusted as can the scraper and or scarfing process height of this system above (703).

Once the holes are filled with SAP in the SAP pick and place drum (700) they need to be emptied. At low surface speeds of the SAP pick and place drum (700) centrifugal force is adequate enough to empty the holes, however as higher rotational speeds, 20 to 30 degrees may be required to empty the holes which causes the nice profile built in the SAP pick and place drum (700) to not be fully transferred into later processes. As such, the same system used to suck SAP in the holes in the SAP pick and place drum (700) can be used to blow SAP out of the holes. As the vacuum stator (600) is fixed, i.e., none rotational, this device can also be used in reverse by applying air into SAP pick and place drum (700).

Having a rotational SAP pick and place drum (700) which rotates in the same direction as the air flow in which the SAP is being discharged, and/or, the nonwoven or tissue substrate, allows the very accurate pick and place of SAP particles, and, with the exact location and size being defined by the location and size of the holes within the SAP pick and place drum (700).

A significant embodiment of this invention however is the ability to deliver more than one variation of SAP, (SAP type A and SAP type B), and to deliver a discontinuous (or pulsating) flow of SAP granules in a continuous air stream without pulsing and thusly not disturbing the downstream processes by a pulsating air stream. In order to achieve this, vacuum stator (600) is made up of a variety of vacuum zones, and, the inner revolving drum (701) can be machined in a specific way to allow each hole to be controlled independently.

As such, FIG. 4C shows a scenario whereby holes in A have a high level of vacuum when they are traveling through the SAP type A pick up zone, and as the same tie, FIG. 4D shows the holes which would have positive pressure applied from behind to prevent SAP type A from entering these holes. As the holes then are rotated through SAP type B pick up zone, the holes in FIG. 4C would remain with vacuum to prevent SAP type A falling into SAP type B pick up zone, however, the holes in FIG. 4D would have vacuum applied to pick up SAP type B, whilst the holes in FIG. 4B would remain with positive air to prevent SAP type B from filling the holes. As such, FIG. 4F represents the holes which would be filled with SAP as SAP pick and place drum exists the SAP filling processes. FIG. 4A depicts the holes which would have positive pressure applied to empty the holes at the location where discharge is desired.

Figure 9:
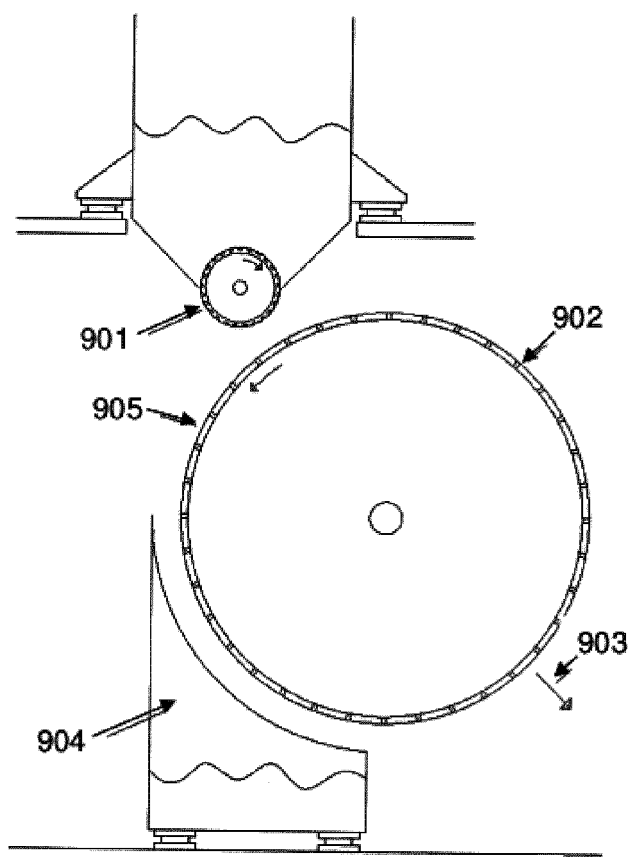
FIG. 9 depicts a further embodiment according to the present invention.
Figure 10:
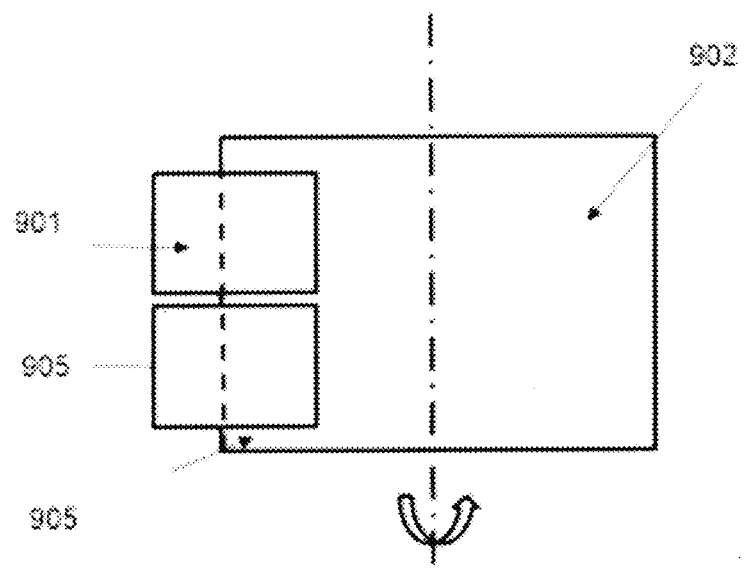
FIG. 10 illustrates a top view of the embodiment depicted in FIG. 9.

Explaining the invention, both apparatus and methodology, FIG. 9 outlines exemplarily in more detail the specific execution of a SAP cascade system. SAP is supplied in a dosing system (901), that, either directly, or indirectly through the use of other apparatus, applies SAP in a cascade over the revolving drum (902). The dosing system (901) would typically be a gravimetric dosing system, but could also be volumetric. The dosing system (901) can comprise a rotating roll with indentations of similar width to the revolving drum (902), but could also be a vibrating feed system or an auger screw supply system. The dosing system (901) can be positioned on a weight-measuring device such as scales to enable the gravimetric dosing to function, but can also be fixed without scales. Also shown in the figure is a potential SAP exiting location (903) where SAP could be applied to a substrate or an air stream or ancillary system such as a transfer drum. A capturing device (904) that captures most or all of the SAP that is not retaining by or within the drum (902). FIG. 9 shows a single cascade system, however multiple cascade systems can be positioned around the revolving drum, either interface with the drum at different angles on the revolving drum (such as at 2 o-clock, 4 o-clock) and can also interface with the drum at similar angles on the revolving drum (such as at 2 o-clock, 4 o-clock) where defined channels feed the different SAP types from dedicated SAP flow channels.

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with a definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An apparatus for applying single or multiple types of SAP granules to an absorbent structure, said apparatus comprising
A—a transfer device, comprising
an essentially static stator defining a rotational axis along with (y-)direction and a radial (r-)direction away from said axis,
an outer revolving drum positioned relative to said stator, the outer revolving drum adapted to be capable of rotating around said stator and comprising holes in a predetermined pattern, which extend essentially (r-) directionally throughout the thickness of said drum,
an inner revolving drum positioned between said outer revolving drum and said stator comprising channels penetrating therethrough, and
a screen positioned between said inner revolving drum and said outer revolving drum, wherein the screen comprises apertures adapted to the particle size of the SAP and preventing at least 95% of said SAP granules from penetrating the screen;
and
B—an SAP granule supply system from the group consisting of:
- at least one SAP granule supply system, operating as a fluidized bed, adapted to provide SAP particles to said holes of said outer revolving drum;
- at least one SAP granule supply system, operating as an SAP cascade system cascading SAP particles on and around the outer revolving drum, the SAP cascade system being adapted to provide SAP particles to said holes of said outer revolving drum;
- multiple supply systems for multiple types of SAP granules, operating as an SAP cascade system cascading SAP particles on and around an outer-revolving drum accessing different vacuum zones at various angles of rotation;
- supply system for multiple types of SAP granules, operating as an SAP cascade system cascading SAP particles on and around an outer revolving drum accessing similar vacuum zones at various angles of rotation where the SAP streams are channeled separately creating cascades of different SAP types flowing parallel to each other;
- an SAP granule supply system, operating as a gravimetric supply process, forming a cascade of SAP where some of a cascade flow is passed across an outer revolving drum where SAP not being held on or within the outer revolving drum is collected by a weighing system;
- an SAP granule supply system, operating as a gravimetric supply process, forming a cascade of SAP where some of a cascade flow is passed across an outer revolving drum where SAP not being held on or within the outer revolving drum is collected by a weight-measuring device, where data from this weight-measuring device is compared with in-feed gravimetric feed supply data to allow actual SAP feed weights to be calculated;

and C—an air vacuum and pressurizing system connected to said stator;
and D—an SAP granule receiving system,
characterized in that
said stator comprises a multiplicity of circumferentially arranged rings and dividers forming chambers, said stator chambers being arranged to be selectively connected to said vacuum and pressurizing system,
and in that said channels of said inner revolving drum exhibit an orientation deviating from the (r)-direction, such that said holes of said outer drum selectively connected via said holes of said inner drum to said chambers of said stator.

2. An apparatus for applying single or multiple types of SAP granules to an absorbent structure according to claim 1, wherein said SAP granule receiving system D is selected from the group consisting of an air duct and an air permeable carrier web.

3. An apparatus for applying single or multiple types of SAP granules to an absorbent structure according to claim 1, wherein said transfer device further comprises a screen positioned between said inner revolving drum and said outer revolving drum whereby said screen is connected to said holes of said outer drum or rotatably mounted.

4. A method for applying singular or multi types of SAP granules into an SAP granule receiving system,
said method comprising the steps of
a) providing an apparatus according to claim 1,
b) providing at least a first plurality of SAP granules;
c) positioning a hole of said outer drum in a proximity of said at least first plurality of SAP granules;
d) providing a vacuum in a predetermined vacuum chamber of said stator;
e) positioning a first channel of said inner drum such that it connects a hole in said outer drum with said vacuum chamber in said stator,
such that SAP granules are positioned into a of said outer drum,
said positioning being supported by said vacuum,
and such said at least 95% of said SAP granules are retained in said holes by a rotating screen;
f) rotating said outer drum through a predetermined angle;
g) expelling said SAP granules from said hole to said SAP granule receiving system.

5. A method for applying singular or multi types of SAP granules into an SAP granule receiving system according to claim 4, wherein said SAP granule receiving system is selected from the group consisting of an air duct and a carrier web.

6. A method for applying singular or multi types of SAP granules into an SAP granule receiving system according to claim 4, wherein said step g) of expelling said SAP granules from said hole to said SAP granule receiving system is executed by connecting said hole in said outer drum to a pressure chamber in said stator by a second channel in said inner drum.

7. A method for applying singular or multi types of SAP granules into an SAP granule receiving system according to claim 6, wherein said granule receiving system is selected from the group consisting of an air duct and a carrier web.

* * * * *